(12) United States Patent
Cobianu et al.

(10) Patent No.: US 8,479,590 B2
(45) Date of Patent: Jul. 9, 2013

(54) SYSTEM FOR MONITORING STRUCTURAL ASSETS

(75) Inventors: Cornel Cobianu, Bucharest (RO); Frank Turnbull, Lanarkshire (GB); Ion Georgescu, Bucharest (RO); Viorel Avramescu, Bucharest (RO)

(73) Assignee: Honeywell International Inc., Morristown, NJ (US)

( * ) Notice: Subject to any disclaimer, the term of this patent is extended or adjusted under 35 U.S.C. 154(b) by 303 days.

(21) Appl. No.: 12/949,113

(22) Filed: Nov. 18, 2010

(65) Prior Publication Data

US 2012/0125118 A1    May 24, 2012

(51) Int. Cl.
*G01N 29/04* (2006.01)
*G01N 3/00* (2006.01)

(52) U.S. Cl.
USPC ............................................. 73/801; 73/803

(58) Field of Classification Search
USPC ........................................ 73/760, 801, 803
See application file for complete search history.

(56) References Cited

U.S. PATENT DOCUMENTS

| | | | |
|---|---|---|---|
| 4,096,740 A | 6/1978 | Sallee | |
| 5,944,928 A * | 8/1999 | Seidner | 156/160 |
| 6,029,526 A | 2/2000 | Feldman et al. | |
| 6,907,787 B2 | 6/2005 | Cook et al. | |
| 7,000,298 B2 | 2/2006 | Cook et al. | |
| 7,048,873 B1 * | 5/2006 | Miksic et al. | 252/388 |
| 7,082,835 B2 | 8/2006 | Cook et al. | |
| 7,100,452 B2 | 9/2006 | Marsh | |
| 7,165,455 B2 | 1/2007 | Magee et al. | |
| 7,198,981 B2 | 4/2007 | Avramescu et al. | |
| 7,243,547 B2 | 7/2007 | Cobianu et al. | |
| 7,302,864 B2 | 12/2007 | Liu et al. | |
| 7,380,464 B2 | 6/2008 | Hasken et al. | |
| 7,514,841 B1 | 4/2009 | Cobianu et al. | |

(Continued)

FOREIGN PATENT DOCUMENTS

| | | |
|---|---|---|
| EP | 2056085 | 3/2011 |
| GB | 2285865 | 7/1995 |

(Continued)

OTHER PUBLICATIONS http://en.wikipedia.org/wiki/Surface_acoustic_wave, "Surface Acoustic Wave," 2 pages, Jul. 21, 2010.

(Continued)

*Primary Examiner* — Max Noori
(74) *Attorney, Agent, or Firm* — Seager Tufte & Wickhem LLC.

(57) ABSTRACT

A system for detection of stress and deformation in a structural asset, for instance, one of reinforced concrete. An area on the asset may have a structure interface, such as a patch, attached to it with a fastening mechanism which may be a layer of an epoxy or other material, or be items such as screws, bolts, welds, or the like. One or more surface acoustic wave (SAW) strain sensors may be attached to the interface with an adhesive layer of epoxy or other material, or with mechanical items. Stress may be transmitted by the interface to the strain sensors. The sensors may be interrogated with a wire or wireless reader to obtain strain measurements. The measurements may indicate stress and deformations such as bulges and breaks in the asset. The measurements may also be a basis for determining location and extent of the stress and deformations.

20 Claims, 8 Drawing Sheets

U.S. PATENT DOCUMENTS

| | | | |
|---|---|---|---|
| 7,576,470 B2 | 8/2009 | Kumar et al. | |
| 7,651,879 B2 | 1/2010 | Cobianu et al. | |
| 7,663,290 B2 | 2/2010 | Konishi et al. | |
| 7,679,153 B2 * | 3/2010 | Ito et al. | 257/416 |
| 7,730,772 B2 | 6/2010 | Cook et al. | |
| 7,755,489 B2 | 7/2010 | Georgescu et al. | |
| 7,841,241 B2 * | 11/2010 | Leigh et al. | 73/754 |
| 7,886,607 B2 | 2/2011 | Fink et al. | |
| 7,891,252 B2 | 2/2011 | Cobianu et al. | |
| 2002/0092976 A1 | 7/2002 | Sugai et al. | |
| 2004/0255681 A1 | 12/2004 | Cook et al. | |
| 2005/0231067 A1 | 10/2005 | Cook et al. | |
| 2006/0086188 A1 | 4/2006 | Avramescu et al. | |
| 2006/0130585 A1 | 6/2006 | Magee et al. | |
| 2006/0236782 A1 | 10/2006 | Hasken | |
| 2007/0028692 A1 | 2/2007 | Liu | |
| 2007/0046479 A1 * | 3/2007 | Hines | 340/584 |
| 2007/0068278 A1 | 3/2007 | Liu et al. | |
| 2007/0114889 A1 | 5/2007 | Cobianu et al. | |
| 2007/0126072 A1 | 6/2007 | Cobianu et al. | |
| 2007/0164633 A1 | 7/2007 | Cobianu et al. | |
| 2008/0084135 A1 | 4/2008 | Ramsesh et al. | |
| 2008/0088441 A1 * | 4/2008 | Breed | 340/539.26 |
| 2008/0265711 A1 | 10/2008 | Kumar et al. | |
| 2009/0102317 A1 | 4/2009 | Cobianu et al. | |
| 2009/0115010 A1 | 5/2009 | Fink et al. | |
| 2009/0314104 A1 | 12/2009 | Lohr et al. | |
| 2010/0058834 A1 | 3/2010 | Cobianu et al. | |
| 2010/0102670 A1 | 4/2010 | Kashyap | |
| 2010/0127834 A1 | 5/2010 | Cobianu et al. | |
| 2010/0141087 A1 | 6/2010 | Bostan et al. | |
| 2010/0158071 A1 | 6/2010 | Cobianu et al. | |
| 2010/0253326 A1 | 10/2010 | Koyilothu et al. | |
| 2012/0105175 A1 * | 5/2012 | Clark et al. | 333/195 |

FOREIGN PATENT DOCUMENTS

| | | |
|---|---|---|
| GB | 2298486 | 9/1996 |
| GB | 2349465 | 11/2000 |
| WO | 2006044438 | 4/2006 |
| WO | 2006047259 | 5/2006 |
| WO | 2006047460 | 5/2006 |
| WO | 2006065813 | 6/2006 |
| WO | 2006115561 | 11/2006 |
| WO | 2007024857 | 3/2007 |
| WO | 2007084434 | 7/2007 |
| WO | 2008039824 | 4/2008 |
| WO | 2008073732 | 6/2008 |
| WO | 2010036561 | 4/2010 |

OTHER PUBLICATIONS

Nomura et al., "Wireless Passive Strain Sensor Based on Surface Acoustic Wave Devices," Sensors & Transducers Journal, vol. 90, Special Issue, pp. 61-71, Apr. 2008.

Search Report for Corresponding Application No. PCT/US2011/060680 Dated Jun. 1, 2012.

* cited by examiner

SYSTEM FOR MONITORING STRUCTURAL ASSETS

BACKGROUND

The present system pertains to structural assets and particularly to monitoring their conditions. More particularly, the system pertains to sensor arrangements for determining asset conditions.

SUMMARY

The present disclosure reveals a system and approach for detection of stress and deformation in a structural asset such as one based in concrete. For instance, the asset may be a reinforced concrete pipe. A surface area of the asset may have a structure interface such as a patch or the like attached to it with a fastening mechanism such as a layer of an epoxy or other material. The fastening mechanism may instead be mechanical items such as screws, bolts, welds, or the like. One or more surface acoustic wave (SAW) strain sensors may be attached to the patch. The attachment of sensors may be achieved with an adhesive layer of epoxy or other material, or with mechanical items. Stress in the asset may be transmitted by the interface to the strain sensors. The sensors may be interrogated with a wire or wireless reader to obtain strain measurements. The measurements may indicate stress and deformations such as bulges and breaks in the asset. Analysis of the measurements may determine location and extent of the stress and deformations.

DESCRIPTION

Figure 1:
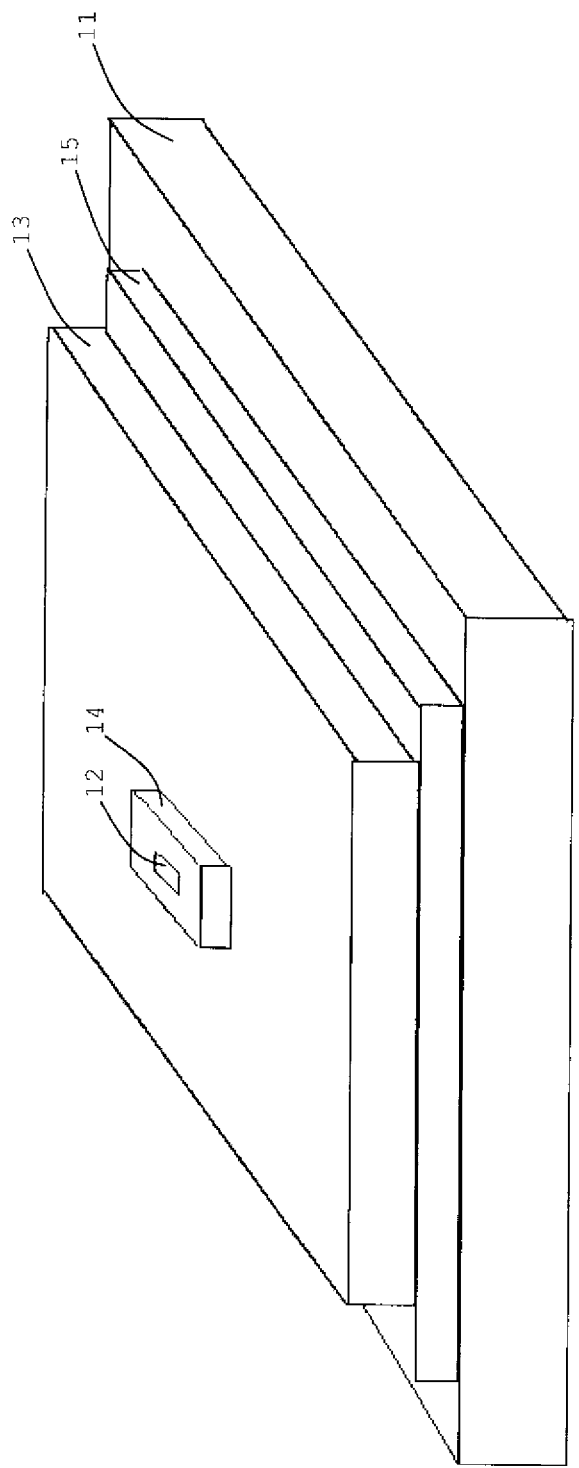
FIG. 1 is a diagram of an application of the present system and approach to monitoring a structural asset.

Early stage detection of stresses and deformation in concrete-based assets by strain measurement may be an important factor in the field of structural health monitoring (SHM) of civil engineering assets (e.g., buildings, bridges, or systems of storm water drain pipes) so that their rehabilitation can be effected before it is too late, in terms of avoiding human lives, or preventing environment or water contamination due to large leakage of potential soil contaminants in the water drain pipe networks. Those assets may be concrete-based, reinforced concrete-based or other material and/or structure based. These assets may generally be regarded as or referred to as structural assets. One or more strain sensors may be used for monitoring structural assets.

A sensing and monitoring solution by the one or more strain sensors may be utilized for detection of mechanical stress, weakness or failure in a civil infrastructure based on, for instance, reinforced concrete as used, for example, in water drain systems, buildings or bridges.

For strain monitoring of the large area-distributed concrete-based assets, major issues may be the type of sensors used with a focus on minimization of their electric power consumption, sensor attachment technology, interrogation electronics of the sensors, and the surveillance concept so that a minimum number of sensors provide reliable monitoring of the asset relative to structural health. The present approach may involve strain detection in concrete based civil engineering assets using surface acoustic wave (SAW) strain gauges. An attachment strategy can be applied to the asset so that the number of sensors may be kept to a minimum while controlling a large area of the asset, and also to reveal electronic interrogation of such SAW sensors either by hand held units, which incorporate reading the sensors by inductive coupling to these sensors, as well as using a near field communication (NFC) principle, or an application of wired electronics.

In order to provide structural health monitoring for controlling the structural health of reinforced concrete-based assets, a system of SAW strain sensors, which can be interrogated by "wired" or wireless electronics, may be implemented. In the wireless case, the inductive coupling-based near field communication may be used. In order to minimize the number of SAW strain sensors for this type of application where large area surfaces of the asset should be kept under stress control, the present approach may be based on using a monitoring beam, patch, tube, strip or plate, as a structure interface, attached to a surface of the asset such as a reinforced concrete structure, where on each patch just a SAW strain gauge or sensor is attached so that the stress which is developed in a certain region of the asset can be transmitted through that patch to be detected by the associated SAW strain sensor attached to the patch. In this approach, the patch may be made of glass fiber reinforced plastic (GFRP). GFRP may be a starting material for such things as beams, strips, patches, tubes and plates. The glass fiber may be randomly embedded in the plastic material for GFRP. The low strength of the pure plastic materials, as well as the low range of linear deformations, under external stress may be eliminated with the use of GFRP.

With respect to other materials that may be used to reinforce plastic, like FRP with carbon, may result in an expensive reinforced plastic. GFRP appears to have low cost, high flexural strength and stress-sensing advantages. Also, GFRP may be epoxy-bonded to a concrete surface. In order to obtain a strong bonding between a GFRP patch and the concrete surface of the asset which is to be monitored, the surfaces of the GFRP patch and concrete should be carefully cleaned (e.g., sandblasting of an asset may establish a fresh clean surface on the asset). A layer of 2-5 mm of epoxy may be applied on the entire cleaned surface of concrete surface for bonding the GFRP patch.

The maximum dimensions of a GFRP item (i.e., length, width, and thickness) may be selected as a function of the patch, tube, strip, plate or beam capability to "collect" the substrate stress at a larger distance, the stress level of interest to be detected in the asset, and as well as the strain gauge or sensor sensitivity, so as to have a single SAW sensor per each sensing patch. In the case of stress in reinforced concrete pipe (RCP), a deformation preceding the bulge formation under the respective GFRP patch may be of interest for detection.

SAW patches may be located from place to place. How many patches are needed may be a matter of trade-off between cost and accuracy of monitoring. Due to the attaching technology, the patch and sensor may become an intrinsic part of the asset, and any local deformation in the asset which is higher than the SAW sensing resolution may be detected.

The present approach may minimize the number of SAW sensors to be used for structural health monitoring of concrete assets, for example, RC (reinforced concrete) pipes having long lengths. The strength capabilities of GFRP may be similar to the reinforced concrete, which is why one could use this approach for rehabilitation of a civil infrastructure. The GFRP may have a linear response on an entire stress range applied to it, up to a final stage where the GFRP becomes brittle.

The SAW sensors may be placed on GFRP beams, strips, patches, tubes and/or plates. A beam, patch, tube, strip, plate and like components may be generally referred to herein with the term "patch" or "item". An appropriate epoxy resin may be used for the attachment of a SAW sensor to a GFRP patch or item.

The present health monitoring structure may be situated on an external portion of or inside the monitored structure.

Installation of a structural health monitoring system based on ultra-low power consumption SAW strain gauge sensors for detecting and measuring the mechanical stress on a large area of a specific civil engineering infrastructure may have a process sequence as noted herein. For an example case, a specific approach for RC pipe monitoring may involve the following steps.

An inspection of the civil engineering infrastructure or concrete asset e.g., an RC pipe, and its associated surroundings may aim at a realization of a risk evaluation for that asset, where the region of potential high stress is to be revealed. However, in some situations, as it is the case of underground ducts for a storm water drain system where soil may expand in time, there appears to be no clear prediction about a location on a pipe where an external load will be applied to the pipe that may exceed a pipe's mechanical strength and thus result in damage. For avoiding water contamination risks due to pipe deterioration, an optimized procedure for the positioning the strain gauges may be provided so that a minimum number of strain sensors can be used for getting a maximum region of the concrete based asset under strain surveillance.

There may be modeling and simulation of a stress distribution in the asset. For the case of an RC pipe with an external load distribution applied in different regions of the pipe, one may identify the amount of load that can cause bulge formation and leakage appearance in the pipe.

There may be modeling of a stress response in different types of stress-transmitting materials as a function of mechanical load applied on the materials. For RC pipes, one may have a selection of glass fiber reinforced plastic plates, tubes, patches, strips and beams and study their response to a mechanical load applied in different positions on them in order to determine the maximal size of stress in correlation with selected sensor sensitivity.

There may be a selection of the beam, patch, tube, plate and strip material type, dimensions, and attachment material or mechanism to which one can firmly attach to an asset. The GFRP beam, patch, tube, plate or strip may be attached to the RC pipe so that stress in the RC pipe can be transmitted with high fidelity to the GFRP item. There may be a selection of sensors. For example, a SAW sensor may be used for strain detection up to its maximum deformation range which for example may be about 2000 microstrains.

There may be surface preparation of a side of a package of a SAW sensor and GFRP item, such as a patch, before applying the epoxy adhesive on the GFRP patch. There may be a deposition of 1-2 mm thick layer epoxy adhesive on the GFR plastic patch. The SAW sensor may be placed on the adhesive for attachment to the GFRP patch.

There may be preparation of the asset's concrete surface as well as that of GFR plastic patch (sandblasting and drying) for obtaining a clean fresh surface. A 3-5 mm thick layer of epoxy adhesive may be deposited on the asset's cleaned surface. Other kinds of adhesives and thicknesses may be utilized.

For attachment of the GFRP patch, carrying the SAW sensor on its other surface, the asset's concrete surface may be covered by epoxy adhesive for the attachment of the patch. There may be a waiting time for curing the adhesive to a solid state of the adhesive layers at the interface between GFRP beam and concrete surface. Electrical connection of the SAW sensor may be made to a power supply for wired interrogation.

The specifics of the descriptions herein, including structure, dimensions and materials, may be examples for illustrative purposes.

FIG. 1 is a diagram of an application of the present system and approach to a concrete asset 11. A SAW sensor 12 may be attached to a GFRP beam, plate, patch, strip or tube 13 with an epoxy 14. The item 13 may be attached to the asset 11 with an epoxy adhesive 15 having a thickness from 2 mm to 5 mm thick applied to a cleaned surface of the asset.

A SAW-GFRP-RCP attachment approach may be noted. The GFRP patch may contain low cost material. The flexural strength of GFRP may be comparable or even higher than that of the steel. A linear (elastic) deformation range of the GFRP patch may extend to a brittle failure mode. A SAW sensor attachment to the GFRP may be preceded by surface preparation of the sensor chip and the GFRP. A SAW-GFRP attachment to an RC pipe or other asset may also be preceded by surface preparation (e.g., surface sandblasting and drying) of the GFRP and asset, and an application of an epoxy between them. The GFRP patch dimensions may be designed based on simulation and experimentation so as to have one SAW sensor per GFRP patch in RCP strain monitoring.

Because of their material properties, GFRP patches may be successfully used in the rehabilitation of a civil engineering infrastructure. The present approach may incorporate the GFR plastic patch containing a SAW sensor on it, with attachment of the patch on virtually its entire surface to the concrete-based asset so that a force, such as a strain or stress, can be conveyed to the SAW sensor.

Figure 2:
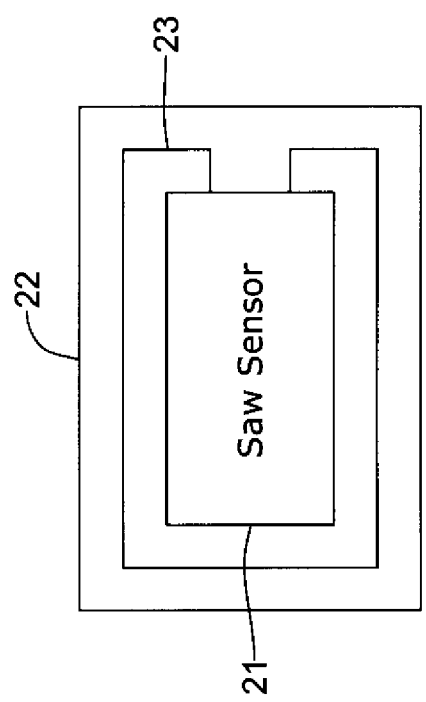
FIG. 2 is a diagram of a surface acoustic wave (SAW) sensor and its antenna on a chip.
Figure 3:
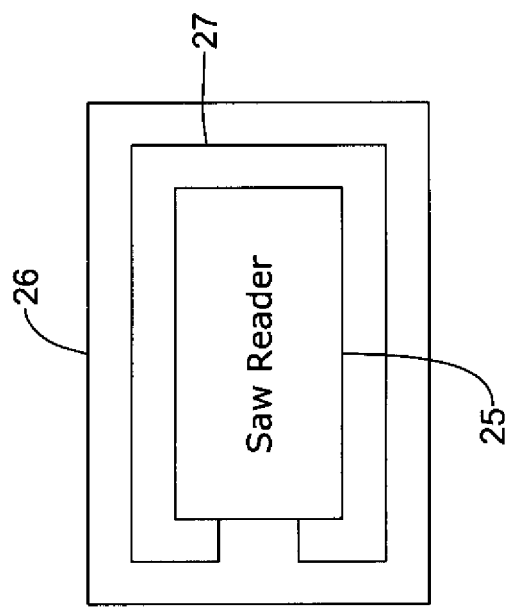
FIG. 3 is a diagram of a SAW sensor reader and its antenna on a chip.

FIG. 2 is a diagram of a SAW sensor 21 situated on a chip 22. Also on chip 22 may be a SAW coil antenna 23 connected to sensor 21. FIG. 3 is a diagram of a SAW reader 25 on a chip 26. Also on chip 26 may be a coil antenna 27 connected to reader 25. Near field communication between the SAW sensor 21 and a SAW sensor reader 25 may be utilized. A principle of near field communication is the inductive coupling between the coil "antenna" 23 of SAW sensor 21 and the coil antenna 27 of reader 25. Reader 25 may be a hand held reader (HHR). In this type of structural health monitoring application, the coil antenna 23 of SAW sensor 21 may be integrated on the same chip 22 with the SAW sensor 21, being located under a glass wall that bonds the chip to its packaging cover.

Sensor reading distance may be below 10 cm depending on the excitation power, antenna size and operating frequency of sensor 21 and reader 25. Each on-site SAW sensor may contain a label for its recognition. A code specific to an identified SAW label may be entered manually by an operator in the hand held reader. This code may be used by the reader to recognize an on-site SAW sensor. The SAW reader may contain a look-up table in its circuit, which provides calibration coefficients for each SAW sensor installed on the asset for strain monitoring. A correct value of the strain reading may be provided by the portable reader after correcting the sensor measurement results with appropriate calibration coefficients for the respective SAW sensor.

A system and approach for continuous monitoring deformation of buried concrete pipelines may be noted. Buried concrete or reinforced concrete pipelines may be used for sewage in urban areas and be exposed to external environmental conditions leading to high compression of the pipeline walls. In extreme situations, the compression may produce deformation bulges on the inner walls that may lead to delamination of concrete from the reinforcement and a fracture of the pipeline wall. This may be a threat to the environment as residual water can contaminate the ground around the cracks or the water can dissolve hazardous substances from the ground surrounding the pipeline and carry these substances in the pipeline to the treatment stations.

To allow appropriate decisions regarding the prevention of environmental contamination, there may be a need for close monitoring of early stage deformations and bulges over the entire length of a pipeline, without previous knowledge of the locations of these bulges.

A "reading" beam may be secured to the inner pipeline wall at discrete fixing points along a longitudinal line (meridian) which transforms and amplifies the deflections due to a bulge to bending and elongation strains at the closest beam fixation points. These strains may be detected and measured using SAW strain sensors, and strain measurements may be transformed into bulge locations and heights using an inversion algorithm or conventional mathematical calculations. The reading beam may have a thin wall open section (U shape) or thin wall closed section (rectangular or circular) and as such can be used as a carrier for sensor cabling and as mechanical protection for sensors and cables in case of pipeline flooding, high velocity flows, or other detrimental activities.

In sum, aspects of the present approach may incorporate fixation of the reading beam to the pipeline wall at discrete points with large gaps between them (implying fast, low-cost installation), using bending of the reading beam as an amplification approach for transforming deflections of the beam due to bulges to strains close to the fixation points (implying good sensitivity for bulge monitoring), using an inverse algorithm giving locations and heights of bulges and performing strain readings at distant points, with a choice of either wireless (and powerless) or wired reading of SAW strain sensors.

There may be several approaches for measuring inner pipe wall deformations. One may consist in laser reading of pipe internal geometry from a robot traveling along the pipeline. While this approach may provide a very accurate measurement of inner wall deformations, it may provide just a periodic inspection and not a continuous monitoring of the pipeline. However, the present approach may give a less accurate deformation and bulge measurement but can provide a continuous monitoring, and could be used to set off alarms indicating a sudden evolution of pipeline damage.

Another approach may consist in using an optical fiber fixed along the pipeline and measuring with optical techniques the straining of the fiber due to pipeline wall deformations and bulges. This approach may be used for continuous monitoring of both the global elongation of a structure (like the sagging of a bridge) and the local straining at critical points of a structure (like plastic strain accumulation due to cyclic loading at critical regions, known beforehand from design or simulation). Nevertheless, this approach may have limitations in that where localized bulges in pipelines do not change significantly the total length of the pipeline, and the bulges may appear at unknown locations along the pipeline.

The present approach may have just a discrete number of fixation or fixed points (with lower installation costs), provide a precise indication of bulge location and height, and have better sensitivity by using the bending of the "reading" beam as a strain amplification technique. A common point of both the reading beam and optical fiber approaches is that they may monitor just a selected meridian along the pipeline and not the entire section of the pipeline. Therefore, in such cases, a preliminary study may be needed to determine the most probable meridian where bulges may appear in response to known pipeline external loading.

In order to provide a continuous monitoring of early stage deformation and bulging of pipeline walls, one may use a small diameter long metallic tube or beam, attached to the pipeline's inner wall along a well chosen meridian, and make measurements with SAW strain sensors of the bending/stretching of the tube or beam due to concrete pipe wall deflection or stretching.

The beam or tube for bulge detection may be made from 1-2 m long pieces that are carried to and assembled on site, and then fixed every 10-20 m on the interior of pipeline walls. SAW sensors may be attached to some of the pieces in a laboratory so that their final location corresponds to maximal bending and stretching strains (in general, close to fixed points of the tube or beam).

Calculations may show that for a 2 cm diameter tube, one might be able to detect a 0.1 cm bulge along the meridian if the fixed points are 10 m apart. Increasing this distance to 30 m in order to decrease installation costs may imply a bulge sensitivity of 1 cm. These values may be compared to an observed value of a bulge of a 10 cm height before concrete delamination.

The interrogation of the sensors may be done in several ways. By carrying a wireless reader through the interior of the pipe, the SAW sensors may be interrogated for readings and the readings be transformed back to pipe deflection and stretching. In this case, the sensors (or at least the antenna) may be located on the exterior of the tube, so that the sensors can be interrogated in a wireless fashion. This approach may be prone to the issue of mechanical damage due to periodical flooding of the pipeline.

In another approach, the SAW sensors used for bulge detection may be mounted inside a hollow tube, and the interrogation may be done through coaxial cables situated in the interior of the tube so that they can also be protected from mechanical damage. These cables may be terminated at the closest manhole, where a technician can plug a reader and interrogate virtually all nearby sensors whose output terminals have been cabled to their measurement points. A length of several hundred meters of the coaxial cable should pose no interrogation problem if the SAW device is designed with 50 ohm input/output impedance (actually a standard to which the SAW systems are often designed).

A determination of maximal tube deflection for bulge detection from bending stresses measured at some points along the tube may involve an inverse approach where one can use robust approaches and algorithms for predicting maximal stresses in a long vibrating pipe when accelerations are measured at some points. An optimization of locations of measuring points may also be part of the present approach.

A choice of the "worst" meridian (i.e., where maximal pipe wall deflections are expected) may be determined based on a finite element simulation model of a buried pipe loaded by a dilatation of the surrounding soil and other loads. The same model may also be used to relate bulge dimensions to concrete failure by crushing/cracking in order to define a safety factor in view of long term monitoring of the pipelines.

An "initial state" of the pipe may be noted. As the pipe walls have curved surfaces, a mounting of a hollow tube along the meridian may impose some initial strains/stresses in the tube. In this case, one may need to do an initial strain/stress reading and use it as a reference point. Then just changes with respect to this reference point may be further noted. This may mean that one is not necessarily able to assess the current status of the existing stress in the pipeline (for example, current stresses in the concrete walls), but just the stresses that have developed after an installation of a SAW-based stress monitoring system.

Figure 4:
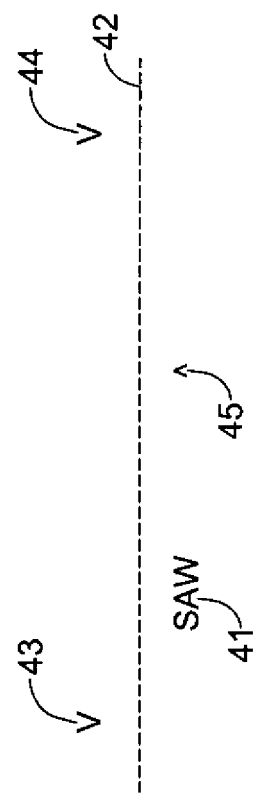
FIG. 4 is a diagram showing a beam attached to a structure at both ends with a stress point at the middle of the beam and a SAW sensor attached near an end of the beam for determining a magnitude of the stress point.

Detection of a bending of an attached beam may be used to measure bulges of a pipeline wall. In a diagram of FIG. 4, a SAW sensor 41 may be placed on a dedicated beam 42. A simple model may be provided to get an order of magnitude effect. An example may involve beam 42 of length L, radius R, clamped at both ends 43 and 44, with a bulge 45 of height h acting in the middle. Maximal bending strains may be close to beam ends 43 and 44, and the maximal strain may be given by "e=6*h*R/(L^2)". For instance, taking L=10 m, h=1 cm, R=1 cm and a 100 MHz SAW sensor 41, may give a frequency shift of approximately 2.5 kHz, which appears reasonable. For L=100 m, frequency shift may be 25 Hz, arguably little too low for some measurement purposes. The frequency shift may be linearly increased by using 400 Mhz SAWs and a larger beam radius.

Figure 5:
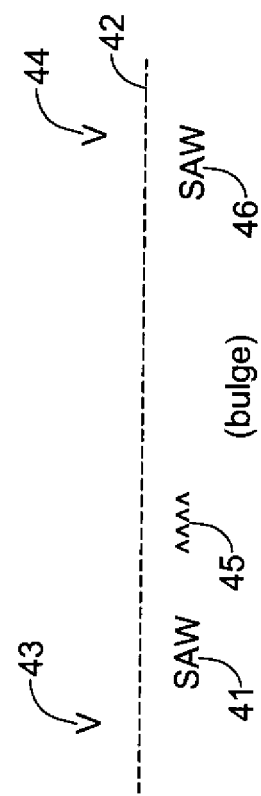
FIG. 5 is a diagram like that of FIG. 4 but has an additional SAW sensor attached near the other end of the beam for determining magnitude and location of the stress point on the beam.

When bulge 45 is not acting in the middle, another SAW sensor in addition to SAW sensor 41 may be utilized. It may be advantageous to put a second SAW sensor 46 close to the other end 44 of beam 42, as shown in a diagram of FIG. 5. Then one may have two measurements for two unknowns, i.e., a position and height of the bulge 45. This example is shown in a diagram of FIG. 5.

Figure 6:
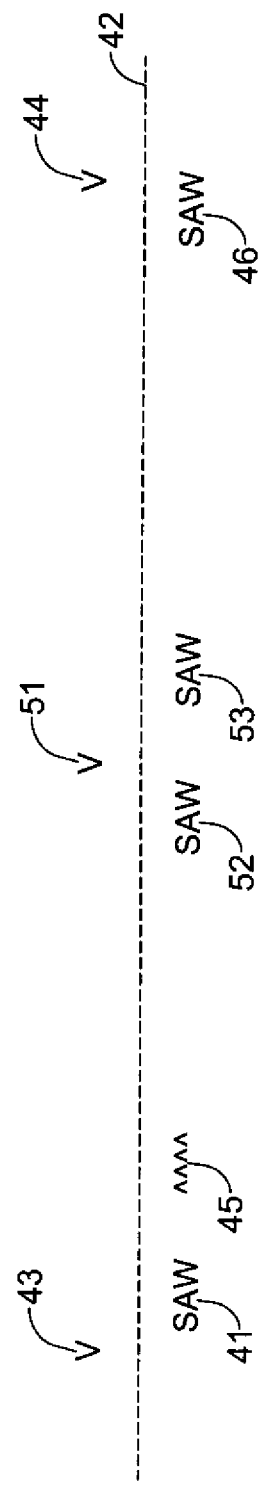
FIG. 6 is a diagram like that of FIG. 5 showing a beam but being further attached to the structure in the middle and having SAW sensors situated on each side of the middle attachment for improved determination of magnitude and location of the stress point on the beam and other possible stress points on the beam.

A further solution may incorporate SAW sensors situated on each side of each attachment such as an example attachment 51 with SAW sensors 52 and 53 as shown in a diagram of FIG. 6. One may devise a robust algorithm that uses virtually all measured strains in order to give locations and heights of several bulges, including bulge 45.

A beam may be made from parts that can be easily transported in the pipe and screwed down, or attached in some other manner, on site. SAW sensors may be attached in a laboratory to some of the beams with a high quality attachment. A high stiffness of the attachment of the beam to the pipe may also be significant for transforming pipe wall displacement to beam bending and SAW sensor strain detection.

The beam can and should be hollow. The wall thickness of the beam may be calculated in order to prevent a plastic collapse of the beam wall close to an attachment for some maximal bulge height. A calculation should also take into account the real longitudinal length of the bulge (in that it is not really a concentrated load).

One may make a simple 3D model of the buried concrete pipe, with the beam attached, and apply a volume increase in the surrounding soil in a limited region, to check the sensing approach under more realistic conditions. This may also provide an optimal location for attaching the beam.

Figure 7:
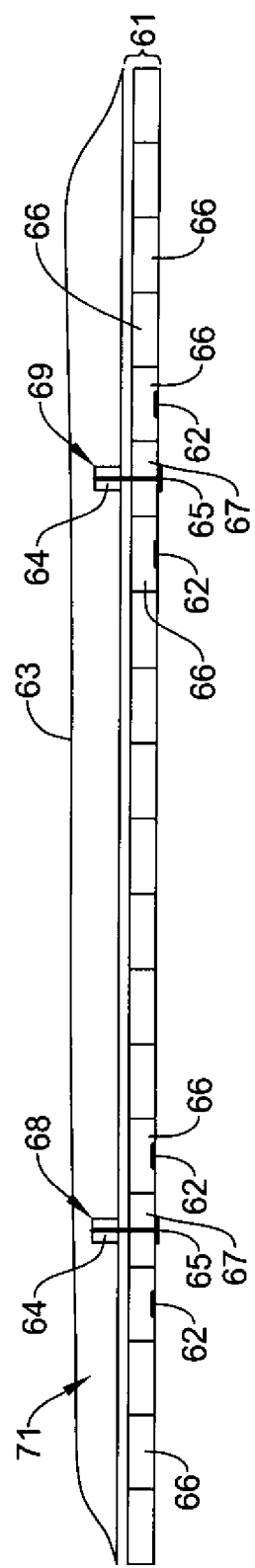
FIG. 7 is a diagram showing an illustrative example of a layout of a multi-segment beam with SAW sensors, which may be attached to a concrete-based asset such as a pipe.

FIG. 7 is a diagram showing an illustrative example of a layout of a multi-segment beam 61 with SAW sensors 62 which may be attached to a concrete based asset such as a pipe 63. Beam 61 may be attached or anchored at several places 64 on a surface of the asset or pipe 63 with, for example bolts 65, or other fastening mechanisms. Beam 61 may be composed of beam segments 66. Segments 66 may be attached to one another in a row to form beam 61 with welding, screwing or another attaching approach. Each of the SAW strain sensors 62 may be attached to a beam segment 66. The SAW sensors 62 may be situated in beam segments 66 adjacent to the segments 67 having bolts 65 which hold certain segments 66 and 67 of beam 61 as a whole to an inside or outside surface of wall 71 of asset or pipe 63. Segments 66 and 67 may be, for instance, one meter long. A distance between locations 68 and 69, where places 64 and bolt 65 attachments of beam 61 are situated, may be about 10 meters apart. Beam 61 may be attached, for example, to the inside wall of pipe 63.

Figure 8:
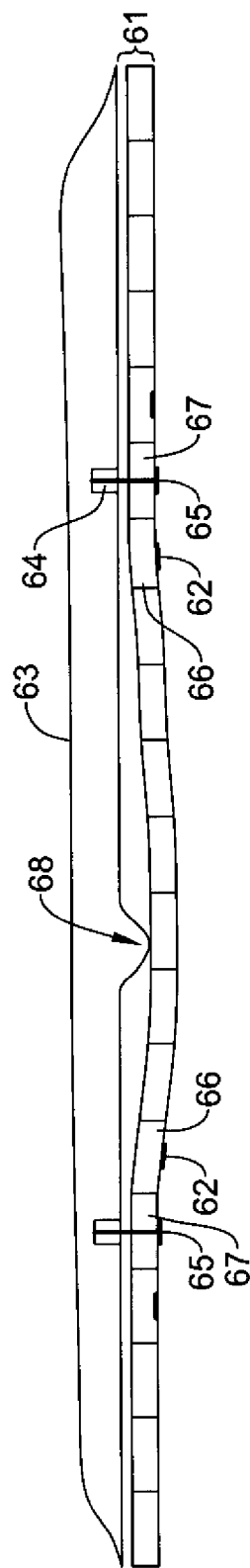
FIG. 8 is a diagram of the SAW sensor arrangement for the concrete-based asset shown in the diagram of FIG. 7 but having a bulge or stress point pushing at a surface of the asset to illustrate an application of the SAW sensor arrangement.

FIG. 8 is a diagram of a layout of the concrete asset or pipe 63 with a bulge 68 pushing in at an outside surface. Bulge 68 at the outside surface may result in a bulge on the inside surface of the concrete asset or pipe 63, which presses against beam 61 causing the beam to be bent out from a straight shape to a curved shape. The bending out of shape of beam 61 may result in strain on the beam segments 66 to which the SAW strain sensors 62 are attached. The strain sensors 62 may output a signal representing the strain on the beam segments 66 where the sensors 62 are situated. The configuration of sensors 62, beam 61, attachment mechanisms 65 and bulge 68 may represent the configuration of sensors 41 and 46, beam 42, attachment mechanisms 43 and 44, and bulge 45 of the diagram in FIG. 5. Similar to calculating the position and height of bulge 45 in FIG. 5, an equation or algorithm may be derived for calculating position and height (or depth) of the bulge 68 from readings of SAW strain sensors 62 in FIG. 8.

In the present specification, some of the matter may be of a hypothetical or prophetic nature although stated in another manner or tense.

Although the present system has been described with respect to at least one illustrative example, many variations and modifications will become apparent to those skilled in the art upon reading the specification. It is therefore the intention that the appended claims be interpreted as broadly as possible in view of the prior art to incorporate all such variations and modifications.

What is claimed is:

1. A system for monitoring strain of a concrete-based asset comprising:
   a monitor patch attached with a first fastening mechanism to a region of a concrete-based asset;
   one or more surface acoustic wave (SAW) strain sensors attached with a second fastening mechanism to the monitor patch; and
   a reader for obtaining strain values from the one or more SAW strain sensors resulting from strain, stress, or both strain and stress transmitted via the monitor patch from the region of the concrete-based asset to the one or more SAW sensors; and
   wherein the monitor patch comprises glass fiber reinforced plastic.

2. A method for monitoring a structural asset, comprising:
   applying a first fastening mechanism to a surface of a structural asset;
   placing an interface structure on the first fastening mechanism;
   applying a second fastening mechanism to a surface of the interface structure;

placing one or more SAW strain sensors on the second fastening mechanism; and selecting one of the one or more SAW strain sensors with a code assigned to a selected SAW strain sensor for obtaining strain measurements indicative of stress in the structural asset from the selected SAW strain sensor; and looking up a table having error correction coefficients to remove errors from the strain measurements from the selected SAW strain sensor wherein:

the interface structure comprises fiber reinforced plastic; and fibers of the fiber reinforced plastic are selected from a group consisting of glass fibers, carbon fibers and aramid fibers.

3. The system of claim 1, wherein:

the first fastening mechanism comprises a layer of epoxy adhesive; and the second fastening mechanism comprises a layer of epoxy adhesive.

4. The system of claim 1, wherein the concrete-based asset is a reinforced concrete pipe.

5. The system of claim 1, wherein the strain values from the one or more SAW sensors cover a range of values of elastic deformation in the concrete-based asset.

6. The system of claim 1, wherein:

the one or more SAW sensors comprise an integrated on-chip antenna; and the reader is a portable unit for obtaining strain values from the one or more SAW sensors via a wireless coupling to the antenna of the one or more SAW sensors.

7. The system of claim 1, wherein:

calibration coefficients for the one or more SAW sensors are stored in a look-up table of the reader; and the reader can make more accurate a strain value from the one or more SAW sensors by correcting the strain value with the calibration coefficients.

8. A method for monitoring a structural asset, comprising:

applying a first fastening mechanism to a surface of a structural asset;

placing an interface structure on the first fastening mechanism;

applying a second fastening mechanism to a surface of the interface structure;

placing one or more SAW strain sensors on the second fastening mechanism; and detecting one or more deformations in the structural asset from strain measurements by the one or more SAW strain sensors; and wherein:

the interface structure transmits stress from the surface of a structural asset to the one or more SAW strain sensors;

the interface structure comprises fiber reinforced plastic; and fibers of the fiber reinforced plastic are selected from a group consisting of glass fibers, carbon fibers and aramid fibers.

9. The method of claim 8, wherein:

the first fastening mechanism is selected from a group consisting of bolts, epoxy adhesives, glues, screws, welds and nails; and the second fastening mechanism from a group consisting of glues, epoxy adhesives, clips, bolts, screws, welds and nails.

10. The method of claim 8, further comprising:

interrogating the one or more SAW strain sensors with a reader to obtain strain measurements indicative of stress in the structural asset;

selecting one of the one or more SAW strain sensors with a code assigned to a selected SAW strain sensor for obtaining the strain measurements with the reader from the selected SAW strain sensor; and looking up a table having error correction coefficients to remove errors from the strain measurements from the selected SAW strain sensor.

11. The method of claim 10, further comprising:

determining a location and height of the one or more deformations in the structural asset from the strain measurements by the one or more SAW strain sensors.

12. The method of claim 8, further comprising developing a model of the structural asset for determining an optimal position of the interface structure on the structural asset, for determining optimal positions for the one or more SAW strain sensors on the interface structure, or for determining an optimal position of the interface structure on the structural asset and determining optimal positions for the one or more SAW strain sensors on the interface structure.

13. A structural asset monitoring system comprising:

an interface structure attached to an area of a surface on a structural asset;

one or more SAW strain sensors attached to the interface structure;

a first mechanism for attaching the interface structure to the area of the surface on the structural asset; and a second mechanism for attaching the one or more SAW strain sensors to the interface structure; and wherein strain measurement readings from the one or more SAW strain sensors are used to determine a deformation in the structural asset, wherein the interface structure includes glass fiber reinforced plastic.

14. The system of claim 13, wherein:

the interface structure comprises fiber reinforced plastic; and fibers of the fiber reinforced plastic are selected from a group consisting of glass fibers, carbon fibers and aramid fibers.

15. The system of claim 13, further comprising:

a reader for interrogating the one or more SAW strain sensors; and wherein each of the one or more SAW strain sensors has a code which is used in the reader to select one of the one or more SAW strain sensors for interrogation of strain measurement readings of a selected SAW strain sensor.

16. The system of claim 13, wherein the structural asset is one of a group consisting of a non-reinforced concrete structure, a reinforced concrete structure, a non-reinforced concrete pipe and a reinforced concrete pipe.

17. The system of claim 13, wherein:

the first mechanism comprises one or more fasteners;

the second mechanism comprises one or more fasteners; and the one or more fasteners are selected from a group consisting of bolts, clips, screws, glues, epoxy adhesives, welds, and nails.

18. The system of claim 13, wherein strain measurement readings from the one or more SAW strain sensors comprise a basis for determining location, height, or location and height of a bulge of a structural asset.

19. The system of claim 13, wherein:

the interface structure is a beam situated along a meridian of the structural asset;

the interface structure is attached to the area of a surface of the structural asset at two or more fixed points; and the one or more SAW strain sensors are attached to the interface structure proximate to one or more of the two or more fixed points, respectively.

20. The system of claim 13, wherein:

the interface structure is a tube;

the one or more SAW strain sensors are situated on an interior of the tube; and signals from the one or more sensors are conveyed from the interior of the tube by conductors through the tube to a location for access by a reader or a processor.

* * * * *